(12) United States Patent
Bystritsky et al.

(10) Patent No.: US 12,257,446 B2
(45) Date of Patent: Mar. 25, 2025

(54) SYSTEMS AND METHODS FOR NEUROMODULATION OF NEURONAL CIRCUITS USING TRANSCRANIAL FOCUSED MICROWAVE PULSES

(71) Applicant: BRAINSONIX CORPORATION, Sherman Oaks, CA (US)

(72) Inventors: Alexander Bystritsky, Sherman Oaks, CA (US); Alexander David Lapidus, Sherman Oaks, CA (US)

(73) Assignee: BRAINSONIX CORPORATION, Sherman Oaks, CA (US)

( * ) Notice: Subject to any disclaimer, the term of this patent is extended or adjusted under 35 U.S.C. 154(b) by 742 days.

(21) Appl. No.: 17/410,572

(22) Filed: Aug. 24, 2021

(65) Prior Publication Data

US 2022/0054853 A1 Feb. 24, 2022

Related U.S. Application Data

(60) Provisional application No. 63/069,588, filed on Aug. 24, 2020.

(51) Int. Cl.
*A61N 5/02* (2006.01)
*A61B 5/00* (2006.01)
(Continued)

(52) U.S. Cl.
CPC ............ *A61N 5/022* (2013.01); *A61B 5/0035* (2013.01); *A61B 5/0036* (2018.08);
(Continued)

(58) Field of Classification Search
CPC .................................. A61N 5/022; A61N 5/04
See application file for complete search history.

(56) References Cited

U.S. PATENT DOCUMENTS 4,343,301 A   8/1982 Indech
5,211,160 A   5/1993 Talish
(Continued)

FOREIGN PATENT DOCUMENTS

EP      0331348      9/1989
JP   2020-501734     1/2020
(Continued)

OTHER PUBLICATIONS

Barlow, et al., The risk of seizure after receipt of whole-cell pertussis or measles, mumps, and rubella vaccine, New England journal of Medicine, vol. 345, No. 9, pp. 656-661 (2001).
(Continued)

*Primary Examiner* — Kaitlyn E Smith
(74) *Attorney, Agent, or Firm* — Schwabe Williamson & Wyatt (57) ABSTRACT

Embodiments provide for systems and methods for modulating activity of a live neuronal circuit within the brain of a mammal. In one example, a method comprises applying a focused microwave pulse to a focal spot corresponding to the live neuronal circuit, while simultaneously monitoring a brain image produced by a brain imaging system. In this way, the focused microwave pulse may be used to transiently modulate the function of the live neuronal circuit, as guided by anatomical and functional information provided via the brain imaging system, useful for both research purposes and for treating psychiatric, neurological and neuroendocrine disorders.

23 Claims, 5 Drawing Sheets

(51) Int. Cl.
  *A61B 5/372* (2021.01)
  *A61N 5/04* (2006.01)
(52) U.S. Cl.
  CPC ............ *A61B 5/0042* (2013.01); *A61B 5/372* (2021.01); *A61N 5/04* (2013.01); *A61B 2560/02* (2013.01)

(56) References Cited

U.S. PATENT DOCUMENTS

| | | |
|---|---|---|
| 5,247,935 A | 9/1993 | Cline |
| 5,275,165 A | 1/1994 | Ettinger |
| 5,282,593 A | 2/1994 | Fast |
| 5,291,890 A | 3/1994 | Cline |
| 5,323,779 A | 6/1994 | Hardy |
| 5,381,794 A | 1/1995 | Tei |
| 5,409,446 A | 4/1995 | Rattner |
| 5,546,438 A | 8/1996 | Hynecek |
| 5,738,625 A | 4/1998 | Gluck |
| 5,752,515 A | 5/1998 | Jolesz |
| 6,066,123 A | 5/2000 | Li |
| 6,088,613 A | 7/2000 | Unger |
| 6,094,598 A | 7/2000 | Elsberry |
| 6,148,225 A | 11/2000 | Kestler |
| 6,198,956 B1 | 3/2001 | Dunne |
| 6,198,958 B1 | 3/2001 | Ives |
| 6,261,231 B1 | 7/2001 | Damphousse |
| 6,267,734 B1 | 7/2001 | Ishibashi |
| 6,348,793 B1 | 2/2002 | Balloni |
| 6,413,216 B1 | 7/2002 | Cain |
| 6,612,988 B2 | 9/2003 | Maor |
| 6,708,051 B1 | 3/2004 | Durousseau |
| 7,283,861 B2 | 10/2007 | Bystritsky |
| 7,300,414 B1 | 11/2007 | Holland |
| 7,427,265 B1 | 9/2008 | Keilman |
| 7,450,985 B2 | 11/2008 | Meloy |
| 7,505,807 B1 | 3/2009 | Kucharczyk |
| 7,896,821 B1 | 3/2011 | Magnin |
| 8,086,296 B2 | 12/2011 | Bystritsky |
| 8,343,083 B1 | 1/2013 | Fencel |
| 9,061,133 B2 | 6/2015 | Wurster |
| 9,630,029 B2 | 4/2017 | Wurster |
| 10,265,497 B2 | 4/2019 | Tsai |
| 10,512,794 B2 | 12/2019 | Wurster |
| 10,792,519 B2 | 10/2020 | Wurster |
| 10,974,078 B2 | 4/2021 | Jordan |
| 11,766,576 B2 | 9/2023 | Jordan |
| 2002/0042121 A1 | 4/2002 | Riesner |
| 2002/0103436 A1 | 8/2002 | Njenanze |
| 2002/0123681 A1 | 9/2002 | Zuk |
| 2002/0127230 A1 | 9/2002 | Chen |
| 2002/0173697 A1 | 11/2002 | Lenhardt |
| 2003/0204135 A1 | 10/2003 | Bystritsky |
| 2004/0048795 A1 | 3/2004 | Ivanova |
| 2005/0020945 A1 | 1/2005 | Tosaya |
| 2005/0240126 A1 | 10/2005 | Roley |
| 2006/0184069 A1 | 8/2006 | Vaitekunas |
| 2006/0191926 A1 | 8/2006 | Ray |
| 2007/0016031 A1 | 1/2007 | Mourad |
| 2007/0299370 A1 | 12/2007 | Bystritsky |
| 2008/0262350 A1 | 10/2008 | Unger |
| 2008/0275340 A1 | 11/2008 | Beach |
| 2009/0005711 A1 | 1/2009 | Konofagou |
| 2009/0112133 A1 | 4/2009 | Deisseroth |
| 2009/0254154 A1 | 10/2009 | De Taboada |
| 2010/0010394 A1 | 1/2010 | Liu |
| 2010/0123529 A1* | 5/2010 | Chang .............. H01P 1/16 |
| | | 333/256 |
| 2011/0092800 A1 | 4/2011 | Yoo |
| 2011/0094288 A1 | 4/2011 | Medan |
| 2011/0166444 A1 | 7/2011 | Elgort |
| 2011/0172653 A1 | 7/2011 | Schneider |
| 2011/0213200 A1 | 9/2011 | Mishelevich |
| 2011/0264012 A1 | 10/2011 | Lautzenhiser |
| 2012/0060847 A1 | 3/2012 | Stratton |
| 2012/0083719 A1 | 4/2012 | Mishelevich |
| 2012/0197166 A1* | 8/2012 | Gertner .............. A61B 6/032 |
| | | 601/3 |
| 2012/0296241 A1 | 11/2012 | Mishelevich |
| 2014/0058293 A1 | 2/2014 | Hynynen et al. |
| 2014/0074181 A1 | 3/2014 | Slutsky |
| 2014/0186423 A1 | 7/2014 | Gelfand |
| 2014/0188011 A1 | 7/2014 | Wurster |
| 2014/0343463 A1 | 11/2014 | Mishelevich |
| 2015/0025421 A1 | 1/2015 | Wagner |
| 2015/0283392 A1* | 10/2015 | Bourke, Jr. .............. A61L 2/10 |
| | | 604/20 |
| 2015/0297176 A1 | 10/2015 | Rincker |
| 2016/0001096 A1 | 1/2016 | Mishelevich |
| 2016/0067526 A1 | 3/2016 | Yang |
| 2017/0105700 A1 | 4/2017 | Bar-Zion |
| 2017/0182339 A1 | 6/2017 | Wurster |
| 2018/0117364 A1 | 5/2018 | Jordan |
| 2018/0304101 A1 | 10/2018 | Yang |
| 2019/0021666 A1 | 1/2019 | Nyhynen |
| 2019/0142513 A1 | 5/2019 | Witte |
| 2020/0121958 A1 | 4/2020 | Wurster |

FOREIGN PATENT DOCUMENTS

| | | |
|---|---|---|
| WO | 2017/195309 A1 | 11/2017 |
| WO | 2018/112269 A1 | 6/2018 |
| WO | 2021/236455 | 11/2021 |
| WO | 2022/046764 | 3/2022 |

OTHER PUBLICATIONS

Bystritsky et al., "A review of low-intensity focused ultrasound pulsation", Elsevier Journal-Brain Stimulation, vol. 4, 2011, pp. 125-136.

Bystritsky et al., A preliminary study of fMRI-guided rTMS in the treatment of generalized anxiety disorder, J Clin Psychiatry, vol. 69, pp. 1092-1098 (Jul. 7, 2008).

Clement et al., A hemisphere array for non-invasive brain therapy and surgery, Physics in Medicine and Biology, vol. 45, No. 12, pp. 3707-3719 (2000).

Colucci et al., Focused ultrasound effects on nerve action potential in vitro, Ultrasound in Med. & Biol., vol. 35, No. 10, pp. 1737-1747 (2009).

Deffieux et al., Low-intensity focused ultrasound modulates monkey visuomotor behaviour, Current Biology, vol. 23, pp. 2430-2433 (Dec. 2, 2013).

Hameroff, et al., Transcranial ultrasound (TUS) effects on mental states: a pilot study, Brain Stimulation, vol. 6, pp. 409-415 (2013).

Jordao, JF et al., "Amyloid-beta plaque reduction, endogenous antibody delivery and glial activation by brain-targeted, transcranial focused ultrasound," Exp Neurol. Oct. 2013; 248: 16-29. Published online May 21, 2013; retrieved from the Internet <https://www.sciencedirect.com/science/article/pll/S0014488613001544?via%3Dihub> <doi: 10.1016/j.expneurol.2013.5.008>.

Kim et al., Estimation of the spatial profile of neuromodulation and the temporal latency in motor responses induced by focused ultrasound brain stimulation, Neurophysiology Neuroreport, vol. 25, No. 7., pp. 475-479 (2014).

Korb, et al., Low-intensity focused ultrasound pulsation device used during magnetic resonance imaging: evaluation of magnetic resonance imaging-related heating at 3 Tesla/128MHz, Neuromodulation, (2013).

Leinenga, G., et al. "Scanning ultrasound removed amyloid-beta and restores memory in an Alzheimer's disease mouse model," Scie Transl Med.; Mar. 11, 2015; 7 (278):278ra33. Retrieved from the Internet <http://stm.sciencemag.org/content/7/278/278ra33> <doi:10.1126/scitranslmed.aaa2512>.

Mehic et al., Increased anatomical specificity of neuromodulation via modulated focused ultrasound, Plos One, vol. 9, Issue 2, pp. 1-13 (Feb. 2014).

Metwally, et al., Influence of the antisotropic mechanical properties of the skull in low-intensity focused ultrasound towards neuromodulation of the brain, 35th Ann Int Conf of IEEE Embs, Osaka, Japan pp. 4565-4568 (Jul. 3-7, 2013).

(56) References Cited

OTHER PUBLICATIONS

Min et al, Focused ultrasound-mediated suppression of chemically-induced acute epileptic EEG activity, BMC Neuroscience; 2011, 12:23, pp. 1-12.

Mulgaonkar et al., A prototype stimulator system for noninvasive low intensity focused ultrasound delivery; Stud Health Technol Inform, vol. 173, 2012, pp. 297-303.

Tufail, et al., Transcranial Pulsed Ultrasound Stimulates Intact Brain Circuits, Neuron, vol. 66, pp. 681-694 (Jun. 10, 2010).

Turfail, et al., Ultrasonic neuromodulation by brain stimulation with transcranial ultrasound, Nature Protocols, vol. 6, No. 9, pp. 1453-1470 (2011).

Tyler et al., Remote excitation of neuronal circuits using low intensity, low frequency ultrasound, Ultrasonic Neurostimulation, vol. 3, No. 10, pp. 1-11 (2008).

Tyler, et al., Remote excitation of neuronal circuits using low-intensity, low-frequency ultrasound, PlosOne, vol. 3, Issue 10, pp. 1-11 (Oct. 2008).

Tyler, W.J., Noninvasive Neuromodulation with Ultrasound? A continuum mechanics hypothesis, pp. 1-12 (2010).

Winhye, et al., Creation on various skin sensations using pulsed focused ultrasound: evidence for functional neuromodulation, International Journal of Imaging Systems and Technology, (Dec. 27, 2013).

Yang, et al., Transcranial focused ultrasound to the thalamus is associated with reduced extracellular GABA levels in rats, Neruopsychobiology, vol. 65, pp. 153-160 (2012).

Yoo, et al., Focused ultrasound modulates region-specific brain activity, Elsevier Journal—NeuroImage, vol. 56, 2011, pp. 1267-1275.

Yoo, et al., Transcranial focused ultrasound to the thalamus alters anesthesia time in rats, Neuroreport, vol. 22(15), pp. 783-787 (Oct. 26, 2011).

Patent Cooperation Treaty: International Search Report and Written Opinion for PCT/US2021/047344 dated Nov. 30, 2021; 15 pages.

Ghodgaonkar, et al., "Microwave Nondestructive Testing of Composite Materials Using Free-Space Microwave Measurement Techniques", Oct. 21, 2000; retrieved from the Internet on Nov. 3, 2021 at <https://www.ndt.net/article/wcndt00/papers/idn251/idn251.htm>.

He, et al., "Overexpression of Slit2 decreases neuronal excitotoxicity accelerates glymphatic clearance, and improves cognition in a multiple microinfarcts model", Aug. 10, 2020; retrieved from the Internet <https://assets.researchsquare.com/files/rs-32713/v2/0bea5b9c-b353-4016-b41c-9640550faae7.pdf?c=1631850797>.

Selbekk, et al., "Ultrasound imaging in neurosurgery: approaches to minimize surgically induced image artefacts for improved resection control"; Acta Neurochir (2013) 155:973-980; retrieved from the Internet on Nov. 3, 2011 at <https:link.springer.com/content/pdf.10.1007/s00701-013-1647-7.pdf>.

\* cited by examiner

SYSTEMS AND METHODS FOR NEUROMODULATION OF NEURONAL CIRCUITS USING TRANSCRANIAL FOCUSED MICROWAVE PULSES

RELATED APPLICATION

The present application claims priority to U.S. Provisional Application No. 63/069,588, filed Aug. 24, 2020, the disclosure of which is hereby incorporated by reference.

TECHNICAL FIELD

Embodiments herein relate to the field of medical diagnosis and treatment, and, more particularly, to diagnosis and treatment of psychiatric, neurological and/or neuroendocrine conditions using a focused microwave pulse delivered to select neural circuits.

BACKGROUND

Neuronal circuits are specific brain centers that are functionally and anatomically connected to one another. Many examples of neuronal circuits involve connections between sub-cortical and cortical brain regions. The precise manner in which neuronal circuits operate is not entirely clear, yet their role has been established in a variety of psychiatric, neurological and related medical conditions.

Existing psychiatric and neurological protocols are not very effective in treating various neurological conditions stemming, at least in part, from abnormal neuronal circuit activity. As a result, a large proportion of the population with such conditions are left with undertreated symptoms and/or undesirable side effects.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

There are a number of neurotherapeutic techniques for non-invasive neuromodulation. Relevant examples of such techniques include repetitive transcranial magnetic stimulation (rTMS), transcranial direct-current stimulation (tDCS), transcranial alternating current stimulation (tACS), laser-based approaches, vagus nerve stimulation (VGS) and low intensity focused ultrasonic pulsation (LIFUP). However, each of the above methodologies have their own insufficiencies. Briefly, rTMS has poor depth penetration, the focus of the stimulation is rather large, and the technique influences/impacts the tissue on the way to the focus. Laser-based approaches have poor penetration and dispersion. DCS, ACS and VNS devices stimulate peripheral nerves and produce non-specific effects on the brain. The focus of LIFUP may be of an overall size (e.g., length, width, diameter, etc.) that does not enable selective stimulation of smaller brain circuits and structures. With further regard to LIFUP, just 10% of the energy may penetrate through thin temporal bone. Accordingly, there is an unmet need for methodology with improved space resolution and depth penetration into the brain with reduced attenuation.

Embodiments herein provide a method for modulating activity of a live neuronal circuit within the brain of a mammal. The method may comprise applying a focused microwave pulse (FMWP) to a focal spot corresponding to the live neuronal circuit, to activate or inhibit the live neuronal circuit. The method may further include monitoring a brain image produced by a brain imaging system during the application of the FMWP. In some examples the mammal may be human, but other mammals (e.g., monkeys, rats, mice, cats, dogs, etc.) are within the scope of this disclosure. Monitoring the brain image may occur in real-time. By real-time, it is meant that raw data (e.g., input) is rapidly processed (e.g., within milliseconds) so that it is available virtually immediately as feedback, or output. The brain imaging system may comprise one or more of a functional magnetic resonance image (fMRI) system, a magnetoencephalograpy (MEG) system, a positron emission tomography (PET) system, a quantitative electroencephalography (qEEG) system, a functional near-infrared spectroscopy (NIRS) imaging system, and/or another suitable imaging system.

In some examples of the method, applying the FMWP may further comprise applying a microwave input signal to a mode converter system. Via the mode converter system, the microwave input signal may be converted (e.g., transformed) into a microwave output signal. The microwave output signal may be then radiated into free space, and focused via a lens in order to apply the FMWP to the focal spot. The mode converter may convert the microwave input signal into the microwave output signal of the axially symmetrical mode to be afterwards focused inside the sample. As a particular example, the input mode (or first mode) is a $TE_{10}$ mode of rectangular waveguide, the second mode is a $TE_{11}$ mode a circular waveguide, and the third mode is a $TE_{01}$ axially-symmetrical mode of the circular waveguide. The mode converter may be connected to a horn that allows for reducing diffraction of the $TE_{01}$ mode while the mode is radiated into free space and transmitted using a lens. The lens focuses the radiation onto the sample under investigation (brain) located inside the MRI chamber, thereby forming a so-called focal spot of high energy concentration inside the sample.

In some examples, the microwave input signal may be of a power level between 2-10 watts. The power level may in some examples be adjusted during the applying the FMWP to the focal spot. The adjusting of the power may comprise increasing the power in some examples, or may comprise decreasing the power in some examples. Such adjusting of the power level may be understood to be based at least in part on the brain image produced via the brain imaging system.

In some examples, the microwave input signal is of a frequency (e.g., carrying frequency) between 2-10 GHz, or between 1-20 GHz. In some examples, the frequency is between 3-9 GHz. Other examples include the frequency being between 4-8 GHz, 4-7 GHz, 4.5-6.5 GHz, etc. In a particular example, the frequency is 5.8 GHz. The frequency may be selected, in some examples, to correspond to attenuation in grey matter of the brain at between 0.7 to 1.0 decibels per 10 centimeters. In some examples, the frequency of the microwave input signal may be adjusted during the applying of the FMWP to the focal spot. The adjusting may comprise increasing the frequency, or may comprise decreasing the frequency. In examples, the adjusting of the frequency may be based at least in part on the brain image produced by the brain imaging system.

In some examples of the method, the focal spot may be of a diameter of 1-2 centimeter or less. In examples, the absorbed power by the brain corresponding to the focused microwave pulse may be 1 watt or less.

In some examples of the method, the method may further comprise adjusting the focal spot via controlling a positioning between the mode converter system and the brain. Controlling the positioning between the mode converter system and the brain may be via a precision mechanical system capable of adjusting the positioning in along three axes (e.g., X, Y, Z axes) in space. It may be understood that in some examples this may enable a scanning of a particular focal region or spot so that the microwave pulse is continually slightly moved within the brain to cover the particular focal region or spot within a predetermined time frame. The shape of such a focal region or spot may comprise three-dimensional space in the brain, for example. The shape may be regular, for example spherical, or may be irregular, depending on the particular application. In some examples, a depth to which the FMWP penetrates the brain may be greater than 5 centimeters (dependent at least in part on microwave carrier frequency and/or power) (e.g., past a base of the skull), and less than 15-20 centimeters.

In an example of the method, the FMWP may comprise an electrical field component and a magnetic field component. Due to the structure of the $TE_{01}$ mode The electric field component at a center of the FMWP may be minimized, such that just the magnetic field component affects the live neuronal circuit to modulate activity of the live neuronal circuit, but the effect of the electrical field component is minimal (e.g., non-existent or in other words, without biological effect).

Another representative embodiment comprises a system for modulating an activity of a live neuronal circuit within the brain of a mammal via a FMWP. Such a system may include a microwave generator, a waveguide, a focusing lens, a brain imaging system, and a display. The system may further comprise a controller. The controller may store instructions in non-transitory memory that, when executed, cause the controller to do one or more of 1) command the microwave generator to produce a microwave input signal that is received by the waveguide and transformed via the waveguide into a microwave output signal, the microwave output signal in turn focused via the focusing lens to yield the FMWP directed to a focal spot within the brain of the mammal to modulate the activity of the live neuronal circuit, 2) control the brain imaging system to record an image of the brain corresponding to at least the live neuronal circuit, and/or 3) present the image on the display for viewing by a user.

In an example of the system, the waveguide may have a profile varied over a length of the waveguide. The profile may comprise a rectangular waveguide input followed by a circular waveguide, the circular waveguide in turn followed by a bent circular waveguide, in examples. In such an example, the circular waveguide may be configured to convert a first $TE_{10}$ of rectangular waveguide mode into a second $TE_{11}$ mode of the circular waveguide and the bent circular waveguide may be configured to convert the second $TE_{11}$ mode into a third $TE_{01}$ axially-symmetrical mode. The system may further comprise a horn coupled to the waveguide downstream of the bent circular waveguide that operates to reduce diffraction of the microwave output signal prior to it being focused via the focusing lens.

In some examples of the system, the brain imaging system is selected from the group consisting of a functional magnetic resonance image (fMRI) system, a magnetoencephalograpy (MEG) system, a positron emission tomography (PET) system, a quantitative electroencephalography (qEEG) system, and a functional near-infrared spectroscopy (NIRS) imaging system. Other examples may use another suitable imaging system and/or a combination of two or more imaging systems. The system may further comprise, in examples, a precision mechanical system to control a microwave system (e.g., including the microwave generator, the waveguide and/or the focusing lens). In such an example, the controller may store further instructions to control the precision mechanical system to adjust the microwave system along three axes (e.g., X, Y, Z) to control a location of the focal spot in the brain, wherein controlling the precision mechanical system may be based at least in part on the image of the brain recorded via the brain imaging system.

In another representative embodiment, a method of treating psychiatric, neurological and neuroendocrine disorders in a mammal is provided. The method may comprise 1) applying a FMWP to a focal spot corresponding to a live neuronal circuit in the brain of the mammal to selectively modulate activity of cells of the live neuronal circuit, and/or 2) monitoring a brain image via a brain imaging system during application of the FMWP, thereby treating the disorder. The mammal may be human in some examples, although other mammals are within the scope of this disclosure. The monitoring of the brain image may occur in real-time.

In an example of the method, the brain imaging system is selected from the group consisting of a functional magnetic resonance image (fMRI) system, a magnetoencephalograpy (MEG) system, a positron emission tomography (PET) system, a quantitative electroencephalography (qEEG) system, and a functional near-infrared spectroscopy (NIRS) imaging system. Other examples may use another suitable imaging system and/or a combination of two or more imaging systems. The disorders include but are not limited to one or more of Obsessive Compulsive Disorder and its spectrum, Post Traumatic Stress Disorder, Depression, Bipolar Disorder, Social Anxiety Disorder, Psychotic Disorder, Panic Disorder, Ticks, Chronic Pain Syndrome, Insomnia, Chronic Fatigue Syndrome, Stress and Obesity.

In some examples of the method, applying the FMWP may comprise applying a microwave input signal to a mode converter system. Via the mode converter system, the method may include converting the microwave input signal into a microwave output signal. The microwave output signal may be radiated into free space, and focused via a lens to thereby apply the FMWP to the focal spot.

In some examples of the method, the method further comprises performing a pre-timed computed tomography (CT) scan to determine bone density and structure of the bone surrounding the brain, and relying at least in part on the determined bone density and structure of the bone for applying the FMWP to the focal spot.

In some examples of the method, the method further comprises administering to the mammal a pharmaceutical composition before and/or during applying the FMWP to the focal spot. In some embodiments, the application of FMWP to the focal spot may increase permeability of brain vessels to deliver a medication or biological of the pharmaceutical composition. Additionally, or alternatively, the application of FMWP may interact with magnetic ligands to activate a previously administered medication or biological of the pharmaceutical composition. In embodiments, the pharmaceutical composition may comprise at least one agonist and/or at least one inhibitor of one or more of excitatory amino acid transporters, neutral amino acid transporters, monoamine transporters, GABA transporters, amino acid transporters, glycine transporters, excitatory amino acid receptors, inhibitory amino acid receptors, and monoaminergic receptors.

Another representative embodiment comprises a non-transitory computer-readable storage medium with an executable program stored thereon for modulating activity of a live neuronal circuit within the brain of a mammal, wherein the executable program instructs a microprocessor to perform one or more of 1) sending a first signal or signals to a microwave generator that instructs the microwave generator to produce a microwave input signal that is received by a mode converter system that converts the microwave input signal to a microwave output signal, the microwave output signal then radiated into free space and focused via a lens to yield a FMWP that is applied to a focal spot corresponding to the live neuronal circuit; 2) retrieving an image of the brain from a brain image system during application of the FMWP; and/or 3) sending the image to a display for viewing by a user.

Yet another representative embodiment comprises a device for applying a FMWP to a live neuronal circuit in the brain of a mammal. The device may comprise at least a microwave generator for producing a microwave input signal, a mode converter system for converting the microwave input signal to a microwave output signal, and/or a lens for focusing the microwave output signal.

Figure 1:
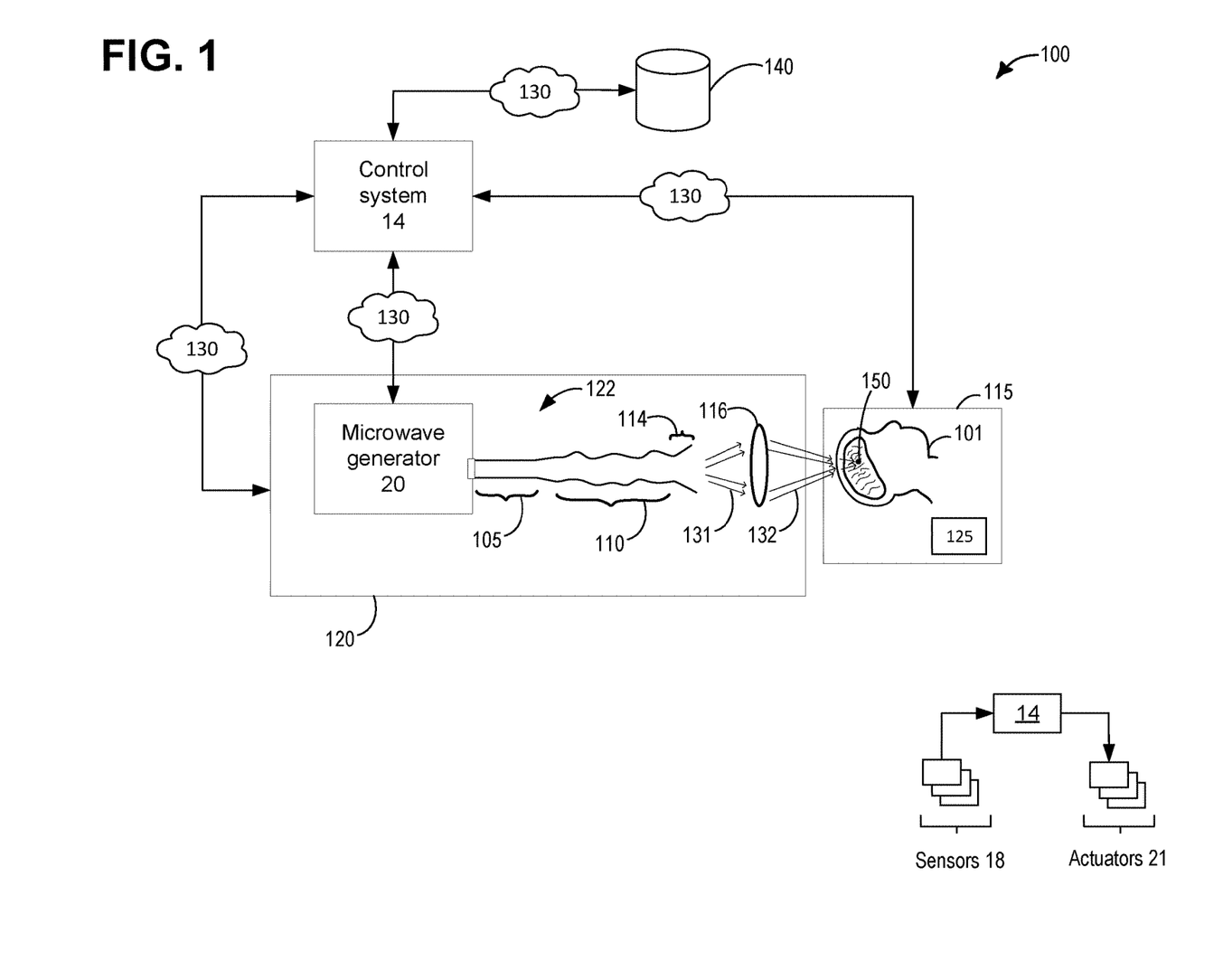
FIG. 1 illustratively depicts a transcranial focused microwave pulse (tFMWP) system for neuromodulation of a live neuronal circuit, in accordance with embodiments.

FIG. 1 depicts a system 100 for providing a transcranial FMWP (tFMWP) to a subject 101. Accordingly, system 100 is referred to herein as a tFMWP system. For brevity, herein a tFMWP is also referred to as a FMWP, and the tFMWP system is also referred to as FMWP system 100. The FWMP may have a duration (e.g., of individual pulses) and a repetition frequency (of repeated pulses). The FWMP may be understood to comprise a carrier microwave frequency of 20 GHz or less. Pulse repetition rate (e.g., repetition frequency), on the other hand, may be between 1 Hz-20 Hz in one example and between 21-1000 Hz in a second example. The first example may comprise an inhibitory FMWP, and the second example may comprise an excitatory FMWP, or vice versa. Thus, it may be understood that the carrier microwave frequency (e.g., 20 GHz or less, for example 10 GHz or less) may be many orders greater than the pulse repetition rate (e.g., between 1 Hz and 1000 Hz). Furthermore, the pulse width may be between 0.5 ms and 1000 ms, with a stimulation duration ranging from 2 seconds to 10 minutes. In some examples, such stimuli may be repeated any number of times (e.g., several) to achieve a desired effect. The subject 101 may in some examples be a subject suffering from a psychiatric, neurological or neuroendocrine disorder, or some combination. In other examples the subject may not have a discernable disorder, but may be a part of a research study, for example. Other examples are within the scope of this disclosure, such as improving some aspect of brain function (e.g., short-term or long term memory, among others). A brain imaging system 115 may be included as a part of FMWP system 100, and the subject 101 may at least partially reside within brain imaging system 115 so that a brain image pertaining to brain activity may be captured. The brain imaging system 115 may include one or more of a functional magnetic resonance image (fMRI) system, a magnetoencephalography (MEG) system, a positron emission tomography (PET) system, a quantitative electroencephalography (qEEG) system, a functional near-infrared spectroscopy (NIRS) imaging system, preferably either an fMRI system or a MEG system, or another suitable imaging system.

Briefly, fMRI, is a technique for measuring brain activity. It works by detecting the changes in blood oxygenation and flow that occur in response to neural activity—when a brain area is more active it consumes more oxygen and to meet this increased demand blood flow increases to the active area, according to theory. fMRI can be used to produce activation maps showing which parts of the brain are involved in a particular mental process. PET uses trace amounts of short-lived radioactive material to map functional processes in the brain. When the material undergoes radioactive decay a positron is emitted, which can be picked up by a detector. Areas of high radioactivity are interpreted as being associated with brain activity.

MEG is an imaging technique used to measure the magnetic fields produced by electrical activity in the brain via extremely sensitive devices known as superconducting quantum interference devices (SQUIDs). These measurements are commonly used in both research and clinical settings. There are many uses for the MEG system, including assisting surgeons in localizing a pathology, assisting researchers in determining the function of various parts of the brain, neurofeedback, and others. EEG is the measurement of the electrical activity of the brain by recording from electrodes placed on the scalp. The resulting traces are known as an electroencephalogram EEG and represent an electrical signal from a large number of neurons. EEGs are frequently used in experimentation because the process is non-invasive to the research subject. The EEG is capable of detecting changes in electrical activity in the brain on a millisecond-level. It is one of the few techniques available that has such high temporal resolution. NIRS is an optical technique for measuring blood oxygenation in the brain. It works by shining light in the near infrared part of the spectrum (700-900 nm) through the skull and detecting how much the remerging light is attenuated. How much the light is attenuated depends on blood oxygenation and thus NIRS can provide an indirect measure of brain activity.

Accordingly, whatever the selected brain imaging system for use, the brain imaging system 115 may be comprised of a sub-system referred to herein as a brain mapping system 125. The brain mapping system 125 may be understood to operationally function by processing raw data retrieved via the brain mapping system 125 in order to produce an accurate map of brain activity. The intricate details of how the brain mapping system 125 operates for each different type of brain imaging system mentioned above is beyond the scope of this disclosure. It may be understood that exemplary operational steps of the brain mapping system 125 may include data filtering, performing distortion corrections, head motion corrections, performing statistical analysis, etc.

Control system 14 may be understood to comprise a computing device such as a personal computer, laptop, mobile device and/or other appropriate technology that enables wired or wireless communication between control system 14 and one or more other components of FMWP system 100. As depicted at FIG. 1, control system 14 may in some examples be capable of receiving a signal or signals from one or more sensors 18 associated with FMWP system 100, and sending another signal or signals to one or more actuators 21 of FMWP system 100, according to various embodiments. For example, control system 14 may be capable of retrieving a signal or signals from various sensors 18 of the brain imaging system 115, and may additionally be capable of controlling one or more actuators 21 associated with the brain imaging system. The controlling of actuators 21 may be responsive to sensor 18 information, or other input into control system 14 (e.g., user input). As a representative example, brain imaging system 115 may include a table (not shown) upon which subject 101 lies. The control system 14 may use positional information retrieved from sensors 18 and may control actuators 21 associated with the table, to position the subject 101 at a desired position for the brain imaging operation. In another representative example, control system 14 may be used to control various other aspects of brain imaging system 115, such as controlling the acquisition of brain image data based at least in part on information retrieved from sensors 18 and by controlling one or more actuators associated with image acquisition via brain imaging system 115.

For the sending and retrieving of signal(s) between the control system 14 and various other components (e.g., brain imaging system 115, brain mapping system 125, and others which will be elaborated below) of FMWP system 100, network 130 may be used. Network 130 may include any appropriate network, including an intranet, the Internet, a cellular network, a local area network (LAN), a wide area network (WAN), a personal network or any other such network or combination thereof. Components used for such a system can depend at least in part upon the type of network and/or environment selected. Protocols and components for communicating via such a network are well known and will not be discussed herein in detail. In embodiments, communication over the network 130 are enabled by wired or wireless connections, and combinations thereof. Network 130 includes a wired or wireless telecommunication means by which network systems may communicate and exchange data. For example, network 130 is implemented as, or may be a part of, a storage area network (SAN), personal area network (PAN), a metropolitan area network (MAN), a local area network (LAN), a wide area network (WAN), a wireless local area network (WLAN), a virtual private network (VPN), an intranet, an Internet, a mobile telephone network, such as Global System for Mobile Communications (GSM), General Packet Radio Service (GPRS), cdmaOne, CDMA2000, Evolution-Data Optimized (EV-DO), Enhanced Data Rates for GSM Evolution (EDGE), Universal Mobile Telecommunications System (UMTS), Digital Enhanced Cordless Telecommunications (DECT), Digital AMPS (IS-136/TDMA), and Integrated Digital Enhanced Network (iDEN), Long-Term Evolution (LTE), $3^{rd}$ generation mobile network (3G), 4th generation mobile network (4G), and/or 5th generation mobile network (5G) networks, a card network, Bluetooth, near field communication network (NFC), any form of standardized radio frequency, or any combination thereof, or any other appropriate architecture or system that facilitates the communication of signals, data, and/or messages (generally referred to as data). Throughout this specification, it should be understood that the terms "data" and "information" are used interchangeably herein to refer to text, images, audio, video, or any other form of information that can exist in a computer-based environment.

Control system 14 may, in addition to controlling various operational aspects of brain imaging system, retrieve data from the brain mapping system 125 in order to present the data on a display (see FIG. 2) for viewing by a user of the FMWP system 100. Control system 14 may be coupled to database 140 for storing and retrieving data stored thereon. In some examples database 140 may comprise a cloud-based database. In other examples, database 140 may comprise a networked server or other device capable of storing data retrieved or generated via control system 14, for example a hard drive.

Via network 130, control system 14 may be coupled to a microwave generator 20. One example of such a microwave generator is Berkeley Nucleonics' Model 845 RF Microwave Signal Generator (Berkeley Nucleophonics Corp, San Rafael, CA). The Model 845 generator is a low-noise and fast-switching microwave signal generator covering from VLF to K-band, 100 kHz up to 26.5 GHz (with the option to extend the frequency down to 9 kHz). The Model further offers a wide and accurately-leveled output power range with high spurious suppression, along with advanced frequency synthesis with fractional-N divider that makes for low SSB phase noise and sub-Hertz frequency resolution. The Model 845 is available in 12, 20, & 26.5 GHz frequencies. In addition, the Model 845 can be customized and configured to each user's specific needs. The Model 845 generator is provided as a representative example of the sort of microwave pulse generator that may be used in accordance with embodiments of the present disclosure. However, it may be understood that other microwave generators may be used without departing from the scope of this disclosure.

The microwave generator 20 may be controlled via control system 14 to produce microwaves pulses of a predetermined power and frequency, elaborated in greater detail infra.

Microwave generator 20 may have a waveguide output WR-340 to WR-112 dependent on the operation frequency (e.g., microwave carrier frequency). Microwave Generator 20 may also have a coaxial output with coaxial adapter to the specified waveguide as a part of converter. Waveguide of the specified size as discussed herein may be understood to comprise transverse electric mode $TE_{10}$ as well as rectangular input 105 coupled to mode converter 110. Accordingly, waveguide of the specified size (e.g., WR-340 to WR-112) is in some examples referred to herein as a mode converter system. Mode converter 110 comprises a $TE_{10}$ rectangular to $TE_{11}$ of a circular waveguide to axially symmetrical mode $TE_{01}$ of a circular waveguide. Said another way, the mode converter 110 is an irregular waveguide assembly with a profile varied over the length of the waveguide. It may be understood that such a mode converter 110 is an example, and other options are within the scope of this disclosure. In the present disclosure, a transition to a circular waveguide is used first and then a bent circular waveguide is used to change the mode structure. Via the use of code, the mode converter shape can be optimized to maximize the efficiency of conversion of one mode structure into the other. The bent mode converter converts the $TE_{11}$ of the circular waveguide into the axially symmetrical mode $TE_{01}$ of the circular waveguide. In some examples, the waveguide assembly discussed above may include an attenuator and a power level indicator. While waveguides comprising WR-340 to WR-112 are disclosed above, in some embodiments other examples are within the scope of this disclosure. As one example, a WR-340 to WR-42 mode converter may be utilized. Such an example may be applicable when higher microwave carrier frequencies are used (e.g., about 20 GHz microwave carrier frequency, for example in a range of 15-20 GHz, or 12-20 GHz). A mode converter comprising WR-340 to WR-112 may be applicable when microwave carrier frequencies of 10 GHz or less are used, for example. However, the use of WR-340 to WR-112 with microwave carrier frequencies of greater than 10 GHz is within the scope of this disclosure. Table 1 below shows waveguide parameters relevant to the present disclosure.

TABLE 1

| | Waveguide parameters | | | | | | |
|---|---|---|---|---|---|---|---|
| | Internal dimensions (inches) | | Operating Range | Mode cutoff frequency (GHz) | | | |
| Size | a | b | (GHz) | $TE_{10}$ | $TE_{01}$ | $TE_{11}$ | Peak power |
| WR-340 | 3.400 | 1.700 | 2.20-3.30 | 1.174 | 3.47 | 3.88 | 12.800-17.700 MW |
| WR-112 | 1.122 | 0.4970 | 7.05-10.00 | 5.26 | 11.87 | 12.99 | 1.340-1.710 MW |
| WR-12 | 0.122 | 0.0610 | 60.0-90.0 | 48.37 | 96.75 | 108.17 | 15.900-22.600 KW |

The mode converter 110 is further coupled to horn 114. Horn 114 may be understood to comprise an open ended circular waveguide in which the open end is flared thus adopting the shape of a horn. Examples of horns relevant to the present disclosure include but are not limited to conical horns, pyramidal horns, H-plane sectoral horns, E-plane sectoral horns, among others. It may be understood that the horn allows for reducing diffraction of the $TE_{01}$ mode while the mode is radiated into free space and transmitted using a lens 116. Lens 116 focuses the microwave radiation onto the sample (e.g., skull and brain of subject 101) under investigation positioned within brain imaging system 115. FIG. 1 schematically depicts the unfocused mode 131 prior to lens 116 and the focused mode 132 following lens 116, for reference. Operationally, use of the FMWP system 100 may be in a shielded room or protective caging.

Collectively, the microwave generator 20, waveguide (including horn 114) and lens 116 are herein referred to as microwave generator system 122, or simply microwave system 122. Microwave system 122 may be controlled by a precision mechanical system 120 that enables precise adjustment of the microwave system 122 along three axes (X, Y, Z). It may be understood that the precision mechanical system 120 enables precise positioning of the focal point 150 inside the sample (e.g., brain) in all three dimensions.

The precision mechanical system 120 may include one or more sensors 18 and one or more actuators 21 which enable control system 14 to precisely control the positioning of the microwave system 122. Sensors may include but are not limited to force sensors, light sensors, temperature sensors, contact sensors, proximity sensors (e.g., infrared tranceivers, ultrasonic sensors, photoresistors), distance sensors (e.g., ultrasonic distance sensors, infrared distance sensor, laser range sensor, encoders, stereo camera, etc.), positioning sensors, acceleration sensors, tilt sensors, inertial measurement units (IMUs), gyroscopes, voltage sensors, and/or current sensors, among others. The actuators 21 may include but are not limited to pneumatic actuators, electrical actuators, mechanical actuators, thermal or magnetic actuators, soft actuators, and/or motors, among others. It may be understood that any of the above mentioned sensors and actuators discussed with regard to precision mechanical system 120 may in some examples comprise sensors and actuators that are relied upon for brain imaging system 115. However, it may be understood brain imaging system 115 may in some examples include specific sensors and actuators depending on the particular system selected for use, and which are understood by those in the art to be used with such imaging systems.

Figure 2:
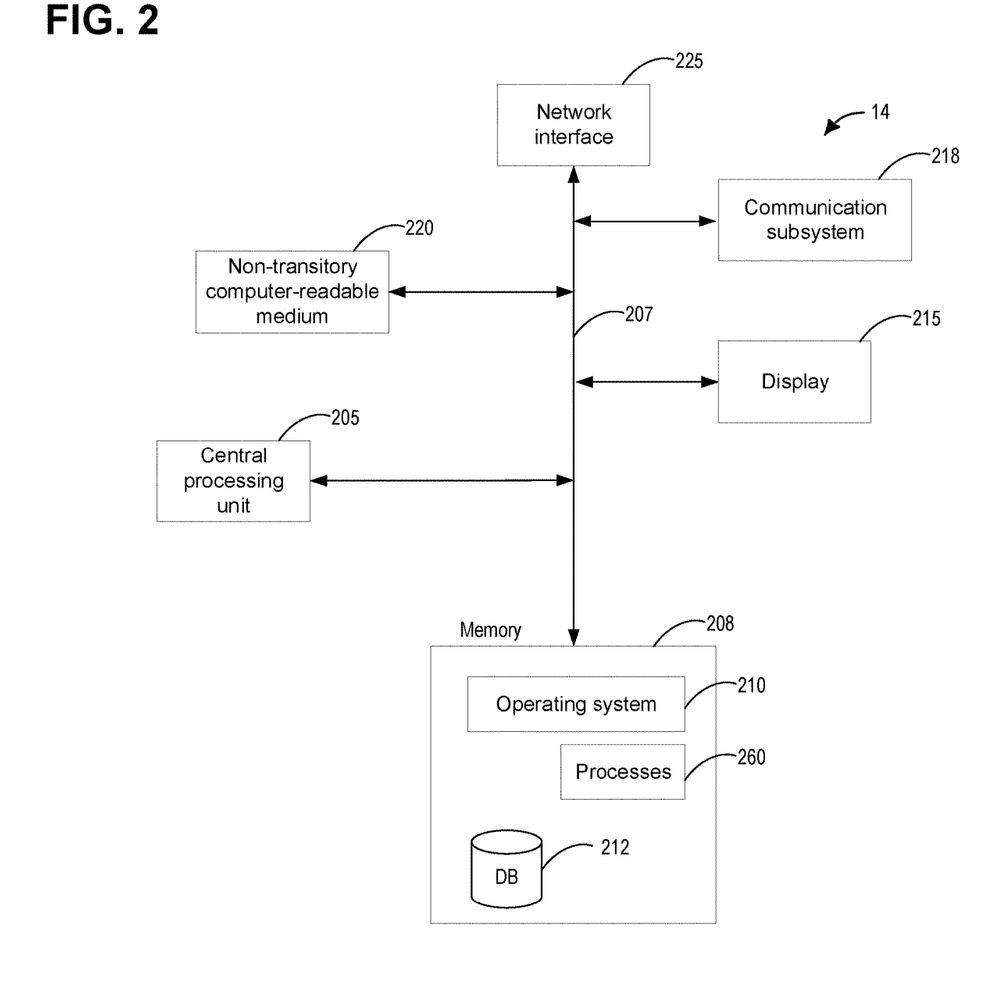
FIG. 2 illustratively depicts an example control system for use with the tFMWP system of FIG. 1, in accordance with embodiments.

Turning to FIG. 2, control system 14 is depicted in greater detail. FIG. 2 depicts a number of components of an exemplary control system 14, in accordance with embodiments of the present disclosure. In various embodiments, control system 14 may comprise a desktop PC, server, workstation, mobile phone, laptop, tablet, set-top box, appliance, and/or other computing device that is capable of performing operations such as those described herein. In some embodiments, control system 14 may include more or fewer components than those shown in FIG. 2, as will be understood by one skilled in the art. Collectively, the various tangible components or a subset of the tangible components may be referred to herein as "logic" configured or adapted in a particular way, for example as logic configured or adapted in a particular way (e.g., as logic configured or adapted with particular software or firmware). In some aspects, logic and memory may be integrated into one or more common devices, such as an application specific integrated circuit or a system on a chip.

In various embodiments, control system 14 may comprise one or more physical and/or logical devices that collectively provide the functionalities described herein. In some examples, control system 14 includes a bus 207 interconnecting several components including a network interface 225, a display 215, a central processing unit 205, a memory 208, a non-transitory computer-readable medium 220, and a communication subsystem 218.

Control system 14 may be configured to execute one or more instructions that are part of one or more applications, services, programs, routines, libraries, objects, components, data structures, or other logical constructions. Such instructions may be implemented to perform a task, implement a data type, transform the state of one or more devices, or otherwise arrive at a desired result. Control system 14 may include one or more processors that are configured to execute software instructions. Additionally or alternatively, the logic subsystem may include one or more hardware or firmware logic machines configured to execute hardware or firmware instructions.

Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration, as an example.

In some embodiments, control system 14 may comprise one or more computing resources provisioned from a "cloud computing" provider. "Cloud computing" or of/in "the Cloud" as used herein refers to a model for enabling ubiquitous, convenient, on-demand network access to a shared pool of configurable computing resources that can be rapidly provisioned and released with minimal management effort or service provider interaction." The defined model comprises five characteristics, which are on-demand self-service, broad network access, resource pooling, rapid elasticity, and measured service. (The NIST Definition of Cloud Computing (NIST Special Publication 800-145)). Clouds can be private, hybrid, or public, and may include Infrastructure as a Service (IaaS), Platform as a Service (PaaS) and Software as a Service (SaaS).

Cloud computing providers include, for example, Amazon Elastic Compute cloud ("Amazon EC2"), provided by Amazon.com, Inc. of Seattle, Washington; Sun cloud Compute Utility, provided by Sun Microsystems, Inc. of Santa Clara, California; Windows Azure, provided by Microsoft Corporation of Redmond, Washington, and the like.

Display 215 may be used to present a visual representation of data held within memory 208 or database 212. Database 212 may in some examples comprise the same database as database 140, however in other examples the databases may be different. As the herein described methods and processes change the data held in the memory 208 or database 212, the state of the information displayed may also change. For example, display 215 may be used to present a visual representation of data using, for example, a "Graphics processing unit" (GPU), a processing unit that comprises a programmable logic chip (processor) specialized for display functions. The GPU may ender images, animations, and video for a computer screen. The GPU may be located on plug-in cards, in a chipset of a motherboard of a computer, or in the same chip as the central processing unit (CPU). The GPU may perform parallel operations on multiple sets of data, and thus may be used as vector processors for non-graphics applications which involve repetitive computations.

Memory 208 generally comprises a random access memory ("RAM") and permanent non-transitory mass storage device, such as a hard disk drive or solid-state drive. Memory 208 stores an operating system 210 as well as processes 260. It may be understood that processes 260 may comprise methods, such as the method depicted at FIG. 3. Software components may be loaded into memory 208 of control system 14 using a drive mechanism (not shown) associated with a non-transitory computer-readable medium 220, such as optical memory (for example CD, DVD, HD-DVD, Blu-Ray Disc, memory stick, and the like) and/or magnetic memory devices (for example hard disk drive, floppy disk drive, tape drive, MRAM, and the like). It may further include devices which are one or more of volatile, non-volatile, dynamic, static, read/write, read-only, random access, sequential access, location addressable, file addressable and content addressable.

Memory 208 also may include database 212. In some embodiments, control system 14 may communicate with database 212 via network interface 225, a storage area network ("SAN"), a high-speed serial bus, and/or via any other suitable communication technology. By way of example, such architectures include Micro Channel Architecture (MCA) bus, Enhanced ISA (EISA) bus, VESA Local Bus (VLB), and Peripheral Component Interconnects (PCI) bus.

In some embodiments, database 212 may comprise one or more storage resources provisioned from a "cloud storage" provider, for example Amazon Simple Storage Service ("Amazon S3"), provided by Amazon.com, Inc. of Seattle, Washington, Google cloud Storage, provided by Google, Inc. of Mountain View, California, and the like. In some embodiments, such databases may be compliant with HIPPA or other government regulatory requirements.

Communication subsystem 218 may be configured to communicatively couple control system 14 with one or more other computing devices. Such connections may include wired and/or wireless communication devices compatible with one or more different communication protocols including, but not limited to, the Internet, a personal area network, a local area network (LAN), a wide area network (WAN) or a wireless local area network (WLAN). For example, wireless connections may be WiFi, Bluetooth®, IEEE 802.11, and the like. Aspects of the present disclosure are described herein with reference to flowchart illustrations and/or block diagrams of methods, apparatus, and computer program products according to the embodiments disclosed herein. It will be understood that each block of the flowchart illustrations and/or block diagrams, and combinations of blocks in the flowchart illustrations and/or block diagrams, can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram blocks.

Those skilled in the art will recognize that optical aspects of implementations may involve optically-oriented hardware, software, and or firmware. The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs, semiconductor devices based around a matrix of configurable logic blocks (CLBs), connected via programmable interconnects. FPGAs as discussed in this context can be reprogrammed to desired application or functionality requirements after manufacturing), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

For example, in some examples, a device such as a computer comprising a compute node may include a processor component and a storage to store instructions that, when executed by the processor component may cause the processor component to retrieve, from one or more storage devices through a network, metadata indicative of organization of data within a data set, map data indicative of organization of multiple data blocks within a data file maintained by the one or more storage devices, wherein the map data may include multiple data blocks within a data file maintained by the one or more storage devices, or wherein the map data includes multiple map entries corresponding to one or more data blocks of the multiple data blocks; and receive, from multiple node devices, indications of which node devices among the multiple node devices are available node devices that are each able to perform a processing task with at least one data set portion of the one or more data set portions.

Those skilled in the art will recognize that it is common within the art to describe devices and/or processes in the fashion set forth herein, and thereafter use standard engineering practices to integrate such described devices and/or processes into larger systems. That is, at least a portion of the devices and/or processes described herein can be integrated into a network processing system via a reasonable amount of experimentation.

Figure 3:
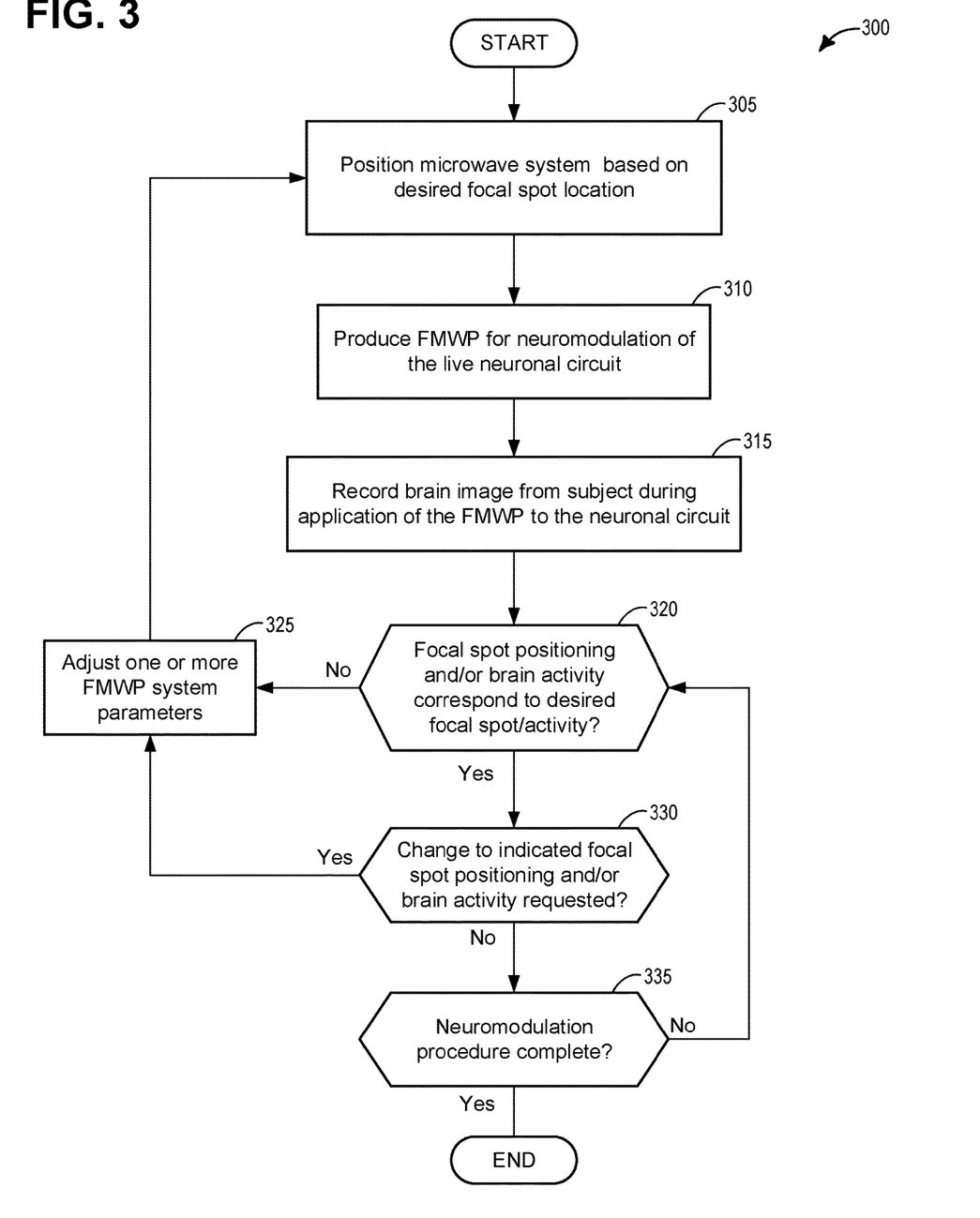
FIG. 3 depicts a high-level method for use of the tFMWP system for neuromodulation of a live neuronal circuit, in accordance with embodiments.

Turning now to FIG. 3, depicted is a high-level example method 300 for delivering a FMWP to a live neuronal circuit in a brain of a mammal, for example a human being. Method 300 is described with reference to the systems depicted at FIGS. 1-2, but it should be understood that similar methods may be used with other systems without departing from the scope of this disclosure. Method 300 may be carried out by control system 14, and may include retrieving information from one or more sensor(s) and controlling a status of one or more actuator(s) of the systems of FIGS. 1-2, to change a state of one or more elements in the physical world. It may be understood that some aspects of method 300 may rely on user interaction with control system 14, however it is possible that an entirety of method 300 may be performed via control system 14 in some examples.

At 305, method 300 includes positioning a microwave system (e.g., the microwave system 122) at a desired position within three-dimensional space. A control system (e.g., control system 14), which is coupled to a brain imaging system (e.g., brain imaging system 115), a microwave system (e.g., microwave system 122) and the precision mechanical system (e.g., precision mechanical system 120), is used to control various parameters surrounding use of a FMWP system (e.g., FMWP system 100). In some examples, one or more brain images may be obtained via the brain imaging system prior to the initial positioning of the microwave system. Information obtained from the initial scans may be used to determine the initial positioning of the microwave system in order to control the FMWP to a desired focal point (e.g., focal point 115) in the brain. For example, the desired focal point may be a particular live neural circuit in the brain of the subject. The focal point may correspond to a live neural circuit that is exhibiting signs of anomalous or abnormal behavior. Additionally or alternatively, the desired focal point may comprise a live neural circuit that is capable of being modulated to influence another brain region that is exhibiting anomalous or abnormal behavior. In still other examples, the focal point may correspond to a live neural circuit whose activity and changes thereof is being investigated by a researcher for research purposes.

Additionally or alternatively, in some examples the initial positioning of the microwave system and desired focal point may be determined at least in part based on a computed tomography (CT) scan, where applicable. For example, a CT scan may provide information about bone density and structure of the skull and brain, and this information may be relied upon for determining where to position the microwave system in order to direct the FMWP to the desired focal point.

To position the microwave system in a manner so as to direct the FMWP to the desired focal point, the control system may retrieve information from one or more sensors (e.g., sensors 18) of the precision mechanical system, and may control one or more actuators (e.g., actuators 21) of the precision mechanical system, in order to control the microwave system to the determined position. In some examples, the precision mechanical system may be controlled at least in part based on input from a user interacting with the control system. For example, a user may interpret initial brain images and/or CT scan(s), and based on the images and/or CT scan(s), input one or more parameters into the control system so that the control system controls the precision mechanical system to a position sufficient to direct the FMWP to the desired focal point. In other examples, it may be understood that minimal or no interaction between a user and the control system may be needed. Specifically, in some examples the control system may include one or more programs stored in memory capable of taking information from brain scans and/or CT scans for a particular subject, and calculating a positioning of the microwave system based that information and a desired/predetermined focal point. In still other examples the subject may be someone who is repeatedly subjected to the FMWP system, for example a subject who requires repeat treatments. In such an example, parameters may be stored, for example at a database (e.g., database 140), and retrieved in order to establish the positioning of the microwave system. In some examples, the control system may include capabilities for learning various parameters based on data acquired for a particular subject over time. For example, the control system may include capabilities pertaining to one or more of artificial intelligence, machine learning and/or deep learning, thus enabling complex patterns and trends obtained from brain imaging scans and FMWP tests to be revealed. Such information may be used by the control system and/or presented to a user (e.g., via display 215) in order to assist in optimizing positioning of the microwave system for performing the method of FIG. 3.

With the positioning microwave system controlled to a particular position, method 300 continues at 310. At 310, method 300 includes providing the FMWP for neuromodulation of the particular live neuronal circuit for which neuromodulation is being utilized. Providing the FMWP may include, via the control system, commanding (e.g., sending a signal or signals to) the microwave generator to produce a particular microwave input signal. The microwave input signal may be selected from a range of about 2-10 watts (W) power and a range of about 2-10 GHz (microwave carrier frequency). The power may be understood to depend on specific MW frequency selected, size of focal point, and penetration depth inside the skull of a mammal. A particular pulse repetition rate (e.g., repetition frequency) may be selected. The pulse repetition rate may be in a range of 1 Hz to 1000 Hz, for example. The microwave input signal is applied to the rectangular waveguide input (e.g., rectangular waveguide input 105) of the mode converter (e.g., mode converter 110). The mode converter system may be a $TE_{10}$ rectangular to $TE_{11}$ of a circular waveguide to axially symmetrical mode $TE_{01}$ of a circular waveguide, however other configurations are within the scope of this disclosure. Via the mode converter (e.g., mode converter 110), the microwave input signal is transformed into a microwave output signal ($TE_{01}$ mode) that is radiated into free space, the diffraction of which is reduced by a horn (e.g., horn 114). The microwave output signal is then focused via a lens (e.g., lens 116) to direct the FMWP to the focal point of the brain under investigation.

At 315, method 300 includes recording one or more brain images from the subject via a brain imaging system (e.g., the brain imaging system 115) during the application of the FMWP to the particular live neuronal circuit. It may be understood that the FMWP may operate to excite one or more neurons associated with the live neuronal circuit. Excitation of a neuron as disclosed herein may be understood to comprise a process of increasing a likelihood of that neuron firing an action potential. Neuron excitation as discussed herein may also be referred to as "activating" a neuron. On the other hand, inhibition of a neuron as disclosed herein may be understood to comprise a process of decreasing a likelihood of that neuron firing an action potential. In some examples, delivering the FMWP to the live neuronal circuit may be understood to excite one or more neurons within that particular neural circuit. The excitation may travel throughout the neural circuit to distal aspects of the neural circuit, or in other words, the effects of the excitation due to the FMWP may be transmitted to other parts of the brain that are connected by way of the neural circuit. Furthermore, there may be other effects of simulating or exciting neurons via the FMWP. Specifically, excitation of one or more neurons may result in neural activity that not only results in action potentials or other forms of excitatory neural transmission, but also may result in the generation of electric field potentials in the extracellular space of the brain. These extracellular fields may influence nearby brain regions in some examples, and may comprise a desired aspect of treatment by the FMWP in some examples.

In some examples, the FMWP may inhibit one or more neurons corresponding to the live neuronal circuit. Inhibition may be understood to decrease the activity of the neuron or neurons for which the FMWP is directed. The inhibition may have downstream effects on the neuronal circuit, similar to those effects described above for excitation. Specifically, inhibition corresponding to a particular neuron or neurons of a live neuronal circuit may reduce a likelihood of downstream neurons firing. Such examples are meant to be illustrative and are not meant to be limiting.

In some examples, the frequency (e.g., microwave carrier frequency) and/or power selected for the microwave input signal may be a determining factor as to whether neuron(s) corresponding to a live neuronal circuit are excited or inhibited. This may in some examples be additionally or alternatively dependent on pulse repetition rate (e.g., repetition frequency). Specifically, certain frequencies (e.g., carrier frequencies) and/or powers of the microwave input signal may correspond to a higher likelihood of the neuron(s) firing, whereas other frequencies (e.g., carrier frequencies) and/or powers of the microwave input signal may correspond to a lower likelihood of the neuron(s) firing.

Additionally or alternatively, pulse repetition rate (e.g., repetition frequency) may influence likelihood of neuron firing.

In some examples, whether neurons of a particular neuronal circuit are excited or inhibited by a FMWP may be influenced by a particular pharmacological treatment given to the subject before and/or during the use of the FMWP system. Pharmacological treatments relevant to the present disclosure include but are not limited to agonists and/or inhibitors of one or more of excitatory amino acid transporters, neutral amino acid transporters, monoamine transporters, GABA transporters, amino acid transporters, glycine transporters, excitatory amino acid receptors, inhibitory amino acid receptors, and monoaminergic receptors.

The recording of the brain image during application of the FMWP may be understood to enable determination of brain activity resulting from the FMWP, and may be used in any number of ways. As one example, the brain image may be used to determine whether the FMWP is being directed at the particular desired focal point, or whether some adjustment is needed. Additionally or alternatively, in some examples the brain image may comprise valuable information regarding brain activity induced by the FMWP, which may be relied upon in terms of a diagnostic, a treatment, or even simply for research purposes into the inner workings of the mind. In terms of treatment, subjecting the subject to FMWPs at particular brain regions may result in some level of relief from a particular condition that the subject is suffering from. For example, the subject may have a neurological, psychological, or neuroendocrine disorder or condition for which one or more symptoms may be alleviated. In some examples, treatments may comprise treatments over a period of time, for example repeat treatments spanning a number of days, weeks, months, years, etc. In other examples, a treatment may comprise a single session of the FMWP system. In additional or alternative examples, a treatment may comprise combining FMWP treatments with other forms of treatments in the forms of pharmaceutical compounds, mental health treatments (e.g., psychotherapy, support groups, complementary and alternative medicine treatments, etc.), or any other relevant form of treatment expected to deliver relief from one or more symptoms associated from a particular disorder that the subject is suffering from.

Proceeding to 320, method 300 includes determining whether the focal spot positioning resulting from the FMWP and as monitored via the brain imaging system corresponds to the focal spot desired/selected. Additionally or alternatively, at 320, method 300 includes determining whether brain activity corresponds to activity expected or desired from the FMWP delivery to the focal spot. In this light, brain activity may comprise activity not just at the focal spot, but downstream activity resulting from the FMWP delivery. Such a determination at 320 may in some examples be made via a user of the FMWP system, for example a user that is monitoring brain images on the display of the control system. In such an example it may be understood that the FMWP system is being operated in an open-loop fashion, where the user makes judgments based on the displayed brain images as to whether the FMWP is being directed to the desired focal point. However, it is also possible that the control system may operate in a closed-loop fashion in some examples, similar to or the same as a proportional integral derivative (PID) controller. For example, the control system may receive information in the form of brain images, and based on the images along with parameters defining the desired focal spot, control the precision mechanical system to move the microwave system 122 to redirect the FMWP to the desired focal spot. It may be understood that, discussed herein, directing the FMWP to the focal spot may comprise a "scanning" of the focal spot with the FMWP. The scanning may comprise closed-loop operation, for example the precision mechanical system 120 may regularly make adjustments so that a particular focal point is "scanned" via the FMWP. In such an example, the focal spot may be some amount larger than a spot that is receiving the microwave pulse, and via closed-loop operation the entirety of the focal spot may be covered in systematic fashion.

Continuing at 320, if it is determined that the focal spot and/or activity do not correspond to the desired focal spot and/or activity, method 300 proceeds to 325. At 325, method 300 includes adjusting one or more FMWP parameters. Examples of parameters that may be adjusted include but are not limited to one or more of positioning of the microwave system, frequency of the microwave input signal (e.g., carrier frequency), power of the microwave input signal, pulse repetition rate (e.g., repetition frequency) and relevant parameters associated with mode conversion.

The adjusting of the one or more parameters may be in some examples via the user of the FMWP system (e.g., in open-loop fashion), whereas in other examples the adjusting may occur in a closed-loop fashion without user input, or with minimal user input (e.g. confirming of a particular adjustment suggested via the control system). Responsive to adjustments being made, method 300 returns to 305 and the method repeats as described above.

Returning to 320, in response to the focal spot positioning and/or brain activity being indicated to correspond to an expected focal spot and/or activity, method 300 continues at 330. At 330, method 300 includes indicating if there is any change requested in regards to the focal spot location and/or brain activity due to the FMWP. For example, a user may monitor brain images and may understand based on training how to more effectively perform neuromodulation in the context of, for example diagnostic methodology and treatments. In other examples, a similar judgement may be made by the control system without user input, based on some level of processing of brain images and further based on one or more of medical history, previous FMWP treatments, particular pharmacological treatments the subject is taking, particular disorder or condition the subject is suffering from, etc. This level of processing may take into account a large number of variables, and may comprise some form of artificial intelligence, deep learning, machine learning, neural networks, or other manner of learning. Such learning may be based on current and prior FMWP treatments of the subject, other similar FMWP treatments of similarly situated individuals (e.g., similar age, condition, mental health history, pharmaceutical treatments, etc.), etc. In still other examples a "change" at 330 may comprise part of a systematic protocol to scan a particular region or focal point to cover an entirety of the particular region or focal point in systematic fashion.

If, at 330, a change is requested, method 300 proceeds to 325 where one or more particular parameters are adjusted to achieve the requested end result. Alternatively, at 330, if no change is requested then method 300 continues at 335. At 335, method 300 includes determining whether the neuromodulation procedure is complete. For example, the neuromodulation procedure may be complete after one or more of some period of time having elapsed, after a user determines it is desirable to finish the procedure, in response to some change in the subject that necessitates discontinuing the procedure (e.g., use of the restroom), after a predetermined number of pulses have been applied to the focal spot, etc. If it is determined at 335 that the neuromodulation procedure is complete, method 300 ends. Otherwise, method 300 returns to step 320, where the method continues in the manner described above.

An aspect of the systems and methods described herein includes the providing of a microwave pulse of a particular repetition rate that is focused and applied to a focal spot in the brain of a mammal. It is herein recognized that more complex pulse sequences may be additionally or alternatively used, without departing from the scope of this disclosure. As one example, a more complex sequence may include a set of any number of pulses (e.g., two or three), repeating with a repetition rate. The pulse form may be, for example, triangular, sawtooth, etc., or a combination. In such examples, the modulation signal for the desired pulse shape may be implemented by a computer-controlled signal generator and applied to a modulation port of the microwave generator (e.g., microwave generator 20). The signal may be synthesized, for example, via a systems engineering software (e.g., LabView, National Instruments, Austin, TX). As one representative example of a two-pulse sequence, a first pulse may comprise a priming pulse for a particular cell or cells, and the second pulse may comprise a stimulating pulse for the same cell or cells. The stimulating pulse may, for example, activate (or inhibit) the cell or cells many times more (e.g., 3×, 5×, 10×, 20× more).

Figure 4A:
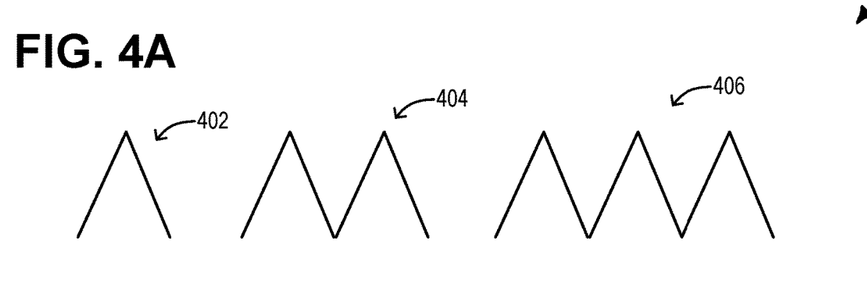
FIGS. 4A-4D depict example microwave pulse shapes that may be used along with the method of FIG. 3.
Figure 4B:
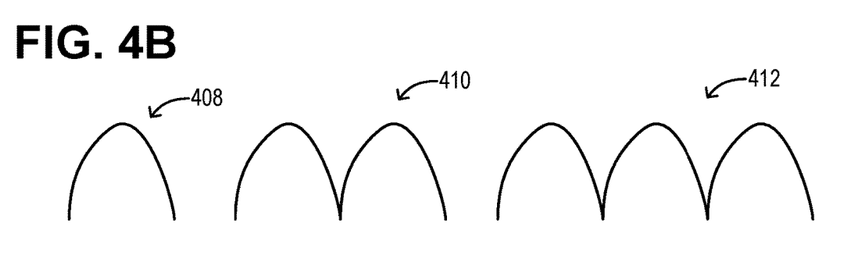
Figure 4C:
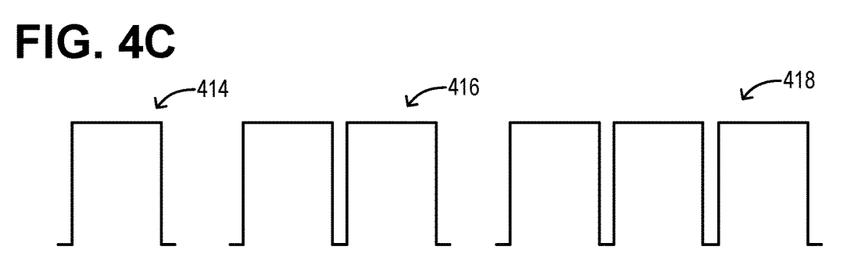
Figure 4D:
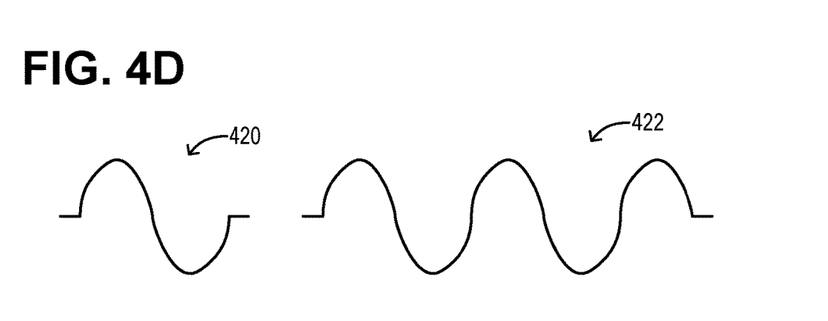

Turning to FIGS. 4A-5D, example illustrations are shown of representative pulses. FIG. 4A depicts monophasic triangle pulse shapes. Depicted for representative purposes is a single triangular pulse 402, a double triangular pulse 404 and a triple triangular pulse 406. For example, a single triangular pulse 402 may be repeated at a particular rate for a particular duration, a double triangular pulse 404 may be repeated at a particular rate for a particular duration, or a triple triangular pulse 406 may be repeated at a particular rate for a particular duration. Similar logic applies to the pulse shapes shown for FIGS. 4B-4C below. FIG. 4B depicts monophasic sinusoidal pulse shapes. Depicted for representative purposes is a single sinusoidal pulse 408, a double sinusoidal pulse 410 and a triple double pulse 412. FIG. 4C depicts monophasic square pulse shapes. Depicted for representative purposes is a single square pulse shape 414, a double square pulse shape 416, and a triple square pulse shape 418. FIG. 4D depicts a single biphasic sinusoidal pulse shape 420, and an extended biphasic sinusoidal pulse shape 422. It may be understood that any of the pulse shapes depicted at FIGS. 4A-4C may be biphasic similar to that depicted at FIG. 4D, without departing from the scope of this disclosure.

Turning now to FIGS. 5A-5D, depicted are examples of binary pulses wherein a first pulse (e.g., first pre-pulse) may prime a neuronal circuit, and before it stops, a second pulse (e.g., second stimulating pulse) may follow. The second pulse may in some examples be larger than the first pulse, whereas in other examples the second pulse may be smaller than the first pulse. While particular examples are shown for illustrative purposes at FIGS. 5A-5D, it may be understood that any of the shapes described above at FIGS. 4A-4D may be used for a sequence that involves a pre-pulse followed by a stimulating pulse, without departing from the scope of this disclosure. While referred to as a "stimulating" pulse, it may be understood that the stimulating pulse may involve exciting or inhibiting a cell or population of neuronal cells.

Figure 5A:
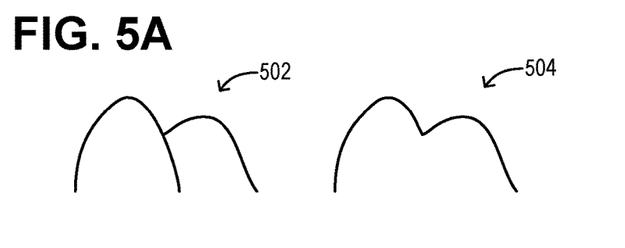
FIGS. 5A-5D depict examples of microwave pulse shapes that may be used along with the method of FIG. 3, and examples of second pulses that follow a first pre-pulse prior to the first pre-pulse stopping.
Figure 5B:
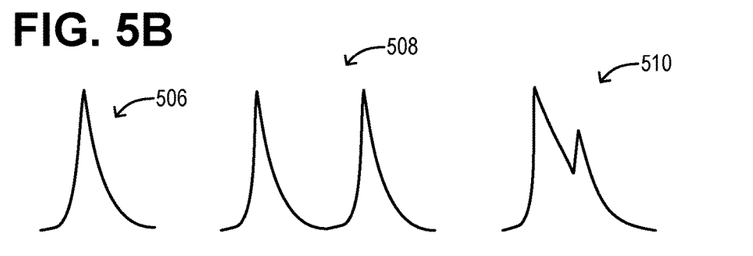

Specifically, FIG. 5A depicts a first example 502 monophasic first pre-pulse followed by a second pulse. FIG. 5A also depicts a second example 504 monophasic first pre-pulse followed by a second pulse. FIG. 5B depicts monophasic sawtooth pulses. Specifically, FIG. 5B depicts a first single sawtooth pulse 506, a second double sawtooth pulse 508 and a third double sawtooth pulse 510. The third double sawtooth pulse 510 illustrates a first pre-pulse followed by a second pulse before the first pre-pulse stops.

Figure 5C:
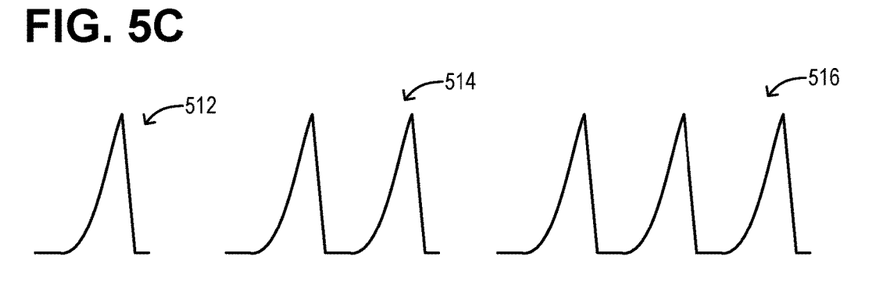
Figure 5D:
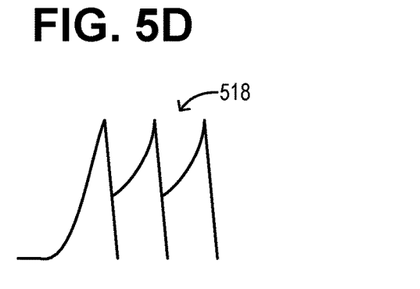

FIG. 5C depicts another example of sawtooth pulse shapes. Specifically, 512 depicts a first single sawtooth pulse 512, a second double sawtooth pulse 514, and a third triple sawtooth pulse 516. The first pulse 512 may be repeated at a particular repetition rate for a particular duration, or the second pulse sequence 514 may be repeated at a particular repetition rate for a particular duration, or the third pulse sequence 516 may be repeated at a particular repetition rate for a particular duration. While a maximum of three pulses for a particular pulse set are illustrated at FIG. 5C and FIGS. 4A-4C, it may be understood that it is within the scope of this disclosure to include any number of pulses in a particular pulse set, that are repeated any number of times. FIG. 5D illustrates an example of a sawtooth pulse sequence 518 where a first pulse is followed by a second pulse that begins prior to the first pulse stopping, and where the second pulse if further followed by a third pulse that begins prior to the second pulse stopping.

It may be understood that the shapes and number/timing of pulses depicted at FIGS. 4A-5D are meant to be illustrative and are not meant to be limiting.

In this way, a tFMWP may be used for purposes of neuromodulation of a live neuronal circuit in a brain of a mammal. The neuromodulation may be used in conjunction with a brain imaging system to control a focal spot in the brain to which the FMWP is applied. By controlling the focal spot that receives the FMWP, activity of a precise region of the brain may be modulated, and brain activity patterns resulting therefrom obtained. The neuromodulation may be useful for treating neurological, neuroendocrine and/or psychiatric disorders, for research purposes and/or for diagnostic purposes.

The FMWP of the present disclosure is provided via a mode converter system that transforms a microwave input signal to a microwave output signal that is then focused by a lens and directed to a focal spot in the brain. The mode converter system is configured to convert the microwave input signal into the microwave output signal in a manner such that a TE01 mode of circular waveguide is radiated into free space and focused by the lens. A technical effect of using such a mode converter system is at least that an average power absorbed by the brain will be not greater than 1-2 W.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

The foregoing described aspects depict different components contained within, or connected with different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

The description of embodiments herein has been presented for purposes of illustration and description. Suitable modifications and variations to the embodiments may be performed in light of the above description or may be acquired from practicing the methods. The described methods and associated actions may also be performed in various orders in addition to the order described in this application, in parallel, and/or simultaneously. The described systems are exemplary in nature, and may include additional elements and/or omit elements. The subject matter of the present disclosure includes all novel and non-obvious combinations and sub-combinations of the various systems and configurations, and other features, functions, and/or properties disclosed.

What is claimed is:

1. A method for modulating activity of a live neuronal circuit within a brain of a mammal, the method comprising:
   generating a focused microwave pulse (FMWP), the FMWP including an electrical field component and a magnetic field component, where the electric field component at a center of the FMWP is minimized;
   applying the FMWP to a focal spot corresponding to the live neuronal circuit, to activate or inhibit the live neuronal circuit, the magnetic field component affecting the live neuronal circuit to modulate activity of the live neuronal circuit and where the electrical field component does not; and
   monitoring a brain image produced by a brain imaging system during the application of the FMWP.

2. The method of claim 1, wherein monitoring the brain image occurs in real-time.

3. The method of claim 1, wherein the brain imaging system is selected from the group consisting of a functional magnetic resonance image (fMRI) system, a magnetoencephalography (MEG) system, a positron emission tomography (PET) system, a quantitative electroencephalography (qEEG) system, and a functional near-infrared spectroscopy (NIRS) imaging system.

4. The method of claim 1, wherein applying the FMWP further comprises:
   applying a microwave input signal to a mode converter system;
   via the mode converter system, converting the microwave input signal into a microwave output signal;
   radiating the microwave output signal into free space; and
   focusing the microwave output signal via a lens to apply the FMWP to the focal spot.

5. The method of claim 4, wherein converting the microwave input signal into the microwave output signal further comprises:
   converting a first transverse electric (TE10) mode of a rectangular waveguide to a second TE11 mode of a circular waveguide, and converting the second TE11 mode to a third TE01 mode of circular waveguide.

6. The method of claim 4, further comprising reducing diffraction of the microwave output signal via a horn prior to focusing the microwave output signal via the lens.

7. The method of claim 4, wherein the microwave input signal is of a power level between 2-10 watts (W) and a frequency of between 2-10 gigahertz.

8. The method of claim 7, wherein the frequency is selected to correspond to attenuation in grey matter of the brain at between 0.7 and 1.0 decibels per 10 centimeters.

9. The method of claim 7, further comprising adjusting at least one of the power level or the frequency during the applying the FMWP to the focal spot.

10. The method of claim 9, wherein adjusting the at least one of the power level or the frequency is based at least in part on the brain image produced by the brain imaging system.

11. The method of claim 1, wherein the focal spot is of a diameter of 1.5 centimeters or less.

12. The method of claim 1, wherein the applying the FMWP is to increase permeability of brain vessels associated with the live neuronal circuit to deliver a medication or biological.

13. A method for modulating activity of a live neuronal circuit within a brain of a mammal, the method comprising:
   generating a focused microwave pulse;
   applying the FMWP to a focal spot corresponding to the live neuronal circuit to interact with magnetic ligands to activate a previously administered medication or biological in the live neuronal circuit.

14. The method of claim 1, further comprising:
   administering to the mammal a pharmaceutical composition before or during applying the FMWP to the focal spot.

15. A system for modulating an activity of a live neuronal circuit within a brain of a mammal via a focused microwave pulse (FMWP), comprising:
   a microwave generator;
   a waveguide assembly having a profile varied over a length of the waveguide assembly, the profile further comprising a rectangular waveguide input followed by a circular waveguide, the circular waveguide followed by a bent circular waveguide, the circular waveguide configured to convert a first transverse electric (TE) mode into a second TE mode and where the bent circular waveguide is configured to convert the second TE mode into a third TE mode, and wherein the first TE mode is a TE10 mode of the rectangular waveguide, the second TE mode is a TE11 mode of the circular waveguide, and the third TE mode is a TE01 mode of the bent circular waveguide;

a focusing lens;

a horn coupled to the waveguide downstream of the bent circular waveguide that operates to reduce diffraction of a microwave output signal prior to the microwave output signal being focused via the focusing lens; and a controller to command the microwave generator to produce a microwave input signal that is received by the waveguide and transformed via the waveguide into a microwave output signal, the microwave output signal in turn focused via the focusing lens to yield the FMWP directed to a focal spot within the brain of the mammal to modulate the activity of the live neuronal circuit.

16. The system of claim 15, further comprising:

a brain imaging system; and a display;

wherein the controller is further to:

control the brain imaging system to record an image of the brain corresponding to at least the live neuronal circuit; and present the image on the display for viewing by a user.

17. The system of claim 16, wherein the brain imaging system is selected from the group consisting of a functional magnetic resonance image (fMRI) system, a magnetoencephalograpy (MEG) system, a positron emission tomography (PET) system, a quantitative electroencephalography (qEEG) system, and a functional near-infrared spectroscopy (NIRS) imaging system.

18. The system of claim 16, further comprising:

a precision mechanical system, wherein the microwave generator, the waveguide and the focusing lens comprise a microwave system; and wherein the controller stores further instructions to:

control the precision mechanical system to adjust the microwave system along three axes to control a location of the focal spot in the brain, wherein controlling the precision mechanical system is based at least in part on the image of the brain recorded via the brain imaging system.

19. One or more non-transitory computer-readable storage media with an executable program stored thereon for modulating activity of a live neuronal circuit within a brain of a mammal, wherein the executable program instructs a microprocessor to perform the operations of:

controlling a microwave generator to produce a microwave input signal that is to be provided to a mode converter system to convert the microwave input signal to a microwave output signal, the microwave output signal to be radiated into free space and focused via a lens to yield a focused microwave pulse (FMWP) that is to be applied to a focal spot corresponding to the live neuronal circuit;

receiving an image of the brain from a brain image system during application of the FMWP;

instructing the mode converter system to control a means for converting the microwave input signal to the microwave output signal so that the microwave output signal corresponds to a predetermined microwave output signal based at least in part on the image received from the brain imaging system; and sending the image to a display for viewing by a user.

20. The one or more non-transitory computer-readable storage media of claim 19, wherein the executable program stores further instructions to specify a power of the microwave input signal and a frequency of the microwave input signal, wherein the power is between 2-10 watts, and wherein the frequency is between 2-10 gigahertz.

21. The one or more non-transitory computer-readable storage media of claim 19 wherein the brain image system is one of a functional magnetic resonance image (fMRI) system, a magnetoencephalograpy (MEG) system, a positron emission tomography (PET) system, a quantitative electroencephalography (qEEG) system, and a functional near-infrared spectroscopy (NIRS) imaging system.

22. The one or more non-transitory computer-readable storage media of claim 19, wherein the executable program stores further instructions that instruct the microprocessor to perform the steps of:

controlling a precision mechanical system coupled to the mode converter and lens, the precision mechanical system having a means for adjusting a positioning between the mode converter and the lens and the brain, wherein the controlling the precision mechanical system is to cause the means for adjusting a distance to operate to set the positioning to a predetermined position along three axes.

23. The one or more non-transitory computer-readable storage media of claim 22, wherein the executable program stores further instructions to send the third signal or signals to the precision mechanical system to control the means for adjusting the distance based at least in part on the image retrieved from the brain imaging system.

* * * * *